(12) United States Patent
Henry et al.

(10) Patent No.: US 9,180,597 B1
(45) Date of Patent: Nov. 10, 2015

(54) MOBILE ANALYTICAL SCREENING, VERIFICATION, AND CONTAINMENT SYSTEM

(75) Inventors: Charles E. Henry, Joppa, MD (US); Monica J. Heyl, Joppa, MD (US); Lisa M. Gremminger, Edgewood, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1659 days.

(21) Appl. No.: 12/140,322

(22) Filed: Jun. 17, 2008

(51) Int. Cl.
  *B25J 21/00* (2006.01)
  *B25J 21/02* (2006.01)
  *B01L 1/00* (2006.01)
  *G01N 30/00* (2006.01)
  *G01N 30/88* (2006.01)
  *A61G 10/00* (2006.01)
  *C12M 1/12* (2006.01)

(52) U.S. Cl.
  CPC .............. *B25J 21/02* (2013.01); *A61G 10/005* (2013.01); *B01L 2200/028* (2013.01); *C12M 37/00* (2013.01); *G01N 30/88* (2013.01); *G01N 2030/8881* (2013.01)

(58) Field of Classification Search
  None
  See application file for complete search history.

(56) References Cited

U.S. PATENT DOCUMENTS

| | | | | |
|---|---|---|---|---|
| 3,907,389 | A * | 9/1975 | Cox et al. | 312/1 |
| 5,316,560 | A * | 5/1994 | Krone-Schmidt et al. | 55/385.2 |
| 5,711,916 | A * | 1/1998 | Riggs et al. | 422/83 |
| 5,730,765 | A * | 3/1998 | Henry et al. | 96/420 |
| 6,428,122 | B1 * | 8/2002 | Henry et al. | 312/1 |
| 6,573,836 | B1 * | 6/2003 | Gitis et al. | 340/603 |
| 6,843,541 | B1 * | 1/2005 | Mills et al. | 312/1 |
| 7,393,373 | B1 * | 7/2008 | Krippner et al. | 55/385.2 |
| 7,964,391 | B2 * | 6/2011 | Bjorndal et al. | 435/288.7 |
| 2003/0157725 | A1 * | 8/2003 | Franzen et al. | 436/171 |
| 2005/0193643 | A1 * | 9/2005 | Pettus | 52/79.1 |
| 2006/0247487 | A1 * | 11/2006 | Arts et al. | 600/21 |
| 2007/0216898 | A1 * | 9/2007 | Gardner, Jr. | 356/301 |
| 2008/0014639 | A1 * | 1/2008 | Vincent et al. | 436/5 |
| 2008/0284289 | A1 * | 11/2008 | Fisher | 312/1 |

* cited by examiner

*Primary Examiner* — Lyle Alexander
*Assistant Examiner* — Jennifer Wecker
(74) *Attorney, Agent, or Firm* — Ulysses John Biffoni

(57) ABSTRACT

This mobile sample isolation and containment system is designed to provide a chemical and biological screening and verification capability within an environmentally-controlled area while minimizing exposure of analytical instruments to contamination. Only those parts of the analytical instrument absolutely necessary for retrieving sample information are disposed within the potentially contaminated enclosure, while other electrical or optical components remain outside said enclosure. The system uses multiple technologies that target, interrogate, and describe the same sample. Therefore, an analyst will not need to remove a hazardous sample from containment before it is identified.

21 Claims, 4 Drawing Sheets

MOBILE ANALYTICAL SCREENING, VERIFICATION, AND CONTAINMENT SYSTEM

GOVERNMENT INTEREST

The invention described herein may be manufactured, used and licensed by or for the U.S. Government.

BACKGROUND

1. Field of the Invention

The invention is in the field of chemical analysis. More specifically, the invention is in the field of mobile chemical analysis containment equipment which can be used for analysis of hazardous and/or toxic chemicals with minimal exposure to analytical instruments.

2. Background of the Invention

Fume hoods and glove boxes are typical laboratory equipment. For safety reasons, many scientists are bringing analytical instrumentation for chemical and biological analysis into their fume hoods and glove boxes at the expense of contaminating the instruments. Having the instrumentation inside the glove boxes creates problems with space, ergonomics, cross-contamination, maintenance, and decontamination (if decontamination is even possible). With mobile laboratories becoming more prominent, this approach will pose safety issues and the movement of contaminated instruments on public roads may possibly even be illegal in certain circumstances.

U.S. Pat. No. 5,730,765, herein incorporated in its entirety by reference, is directed toward a super toxic analytical glove box system. This system is also designed to keep analysis instrumentation off the work surface of the glove box; however, the system only allows for gaseous analysis and is extremely cumbersome.

Therefore, it is desirable to have an analysis and containment system that allows for an open work surface, has instruments that are accessible through the walls of the system, and is easily portable.

SUMMARY OF THE INVENTION

The system of the present invention leaves the already limited area of a glove box or fume hood working surface free for the items that are absolutely necessary and, thus, are more easily maintained. Only those parts of the analytical instruments necessary to retrieve the sample information are disposed within the containment area of the system. Decontamination between samples is rapid. Once unpackaged, the operator can analyze, dilute, aliquot, dispose of, or repackage the sample in the safety of a controlled environment.

DETAILED DESCRIPTION OF THE INVENTION

Figure 1:
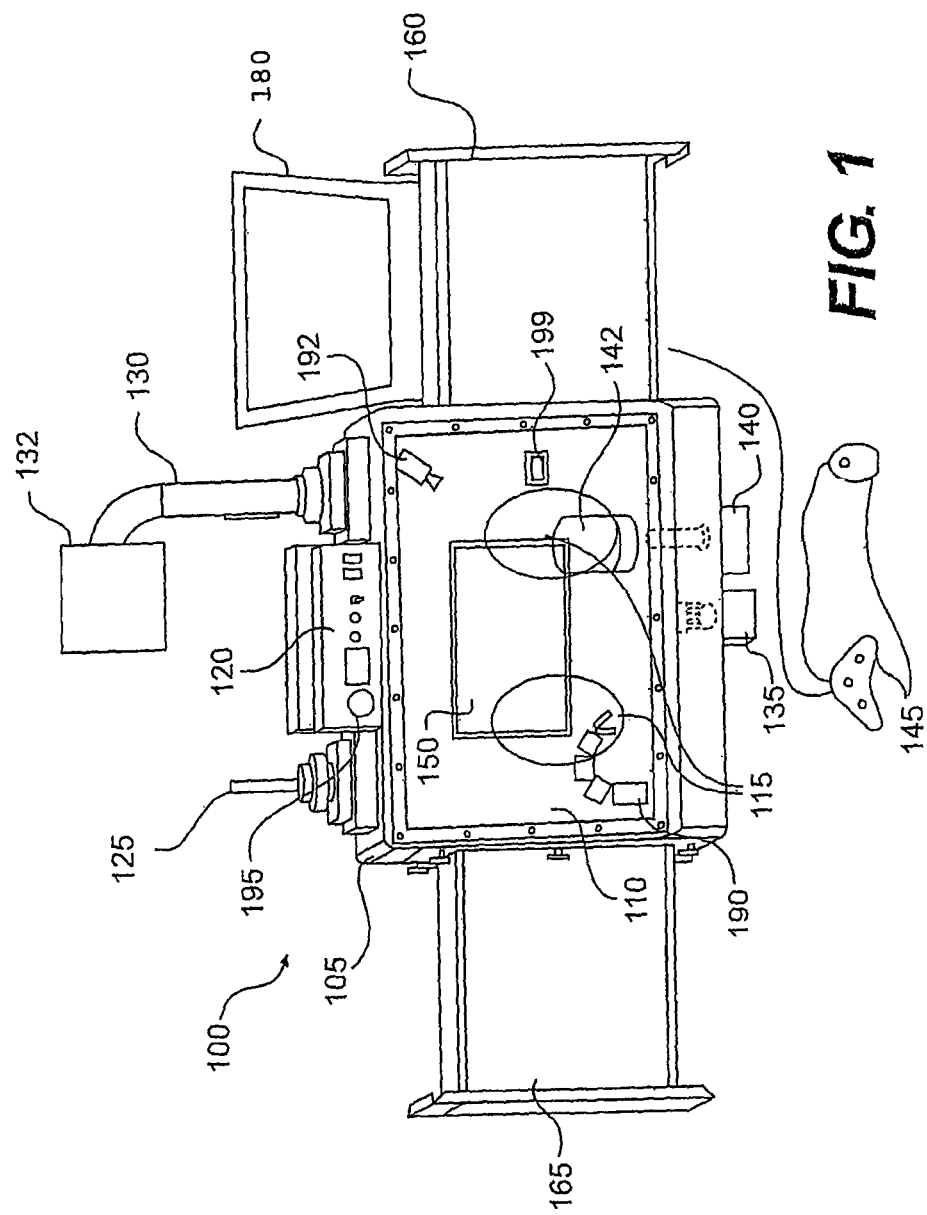
FIG. 1 is an embodiment of the system of the invention.

FIG. 1 shows a mobile containment system 100. Containment system 100 consists of a sealed enclosure 105, such as a class III biosafety cabinet. Sealed enclosure 105 may be of any material, including but not limited to metal, glass, carbon fiber, plastic, fiberglass, etc. Sealed enclosure 105 should be air tight to prevent chemicals from escaping. In certain embodiments, the interior of sealed enclosure 105 may be maintained at a pressure below ambient pressure to prevent contamination from escaping the enclosure 105. In other embodiments, sealed enclosure 105 may be resistant to explosions.

Sealed enclosure 105 may have at least one transparent face 110. While transparent face 110 is shown as the front face of sealed enclosure 105 in FIGS. 1 and 2, transparent face 110 can be any face of sealed enclosure 105. Transparent face 110 may be of any transparent material, including but not limited to glass, plastic, etc. Transparent face 110 is coupled to sealed enclosure 105 by an air tight seal.

Figure 2:
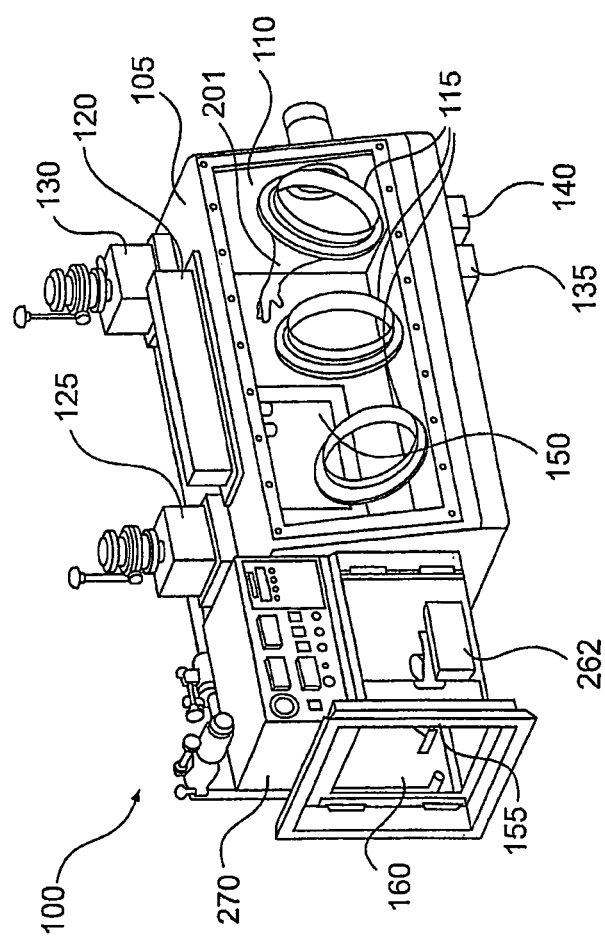
FIG. 2 is a second embodiment of the system of the invention.

Sealed enclosure 105 may additionally have holes 115 through which gloves 201 (shown in FIG. 2) can extend. While holes 115 are shown in transparent face 110, holes 115 may be in any face of sealed enclosure 105. Additionally, holes 115 may be in separate faces of sealed enclosure 105. While two holes 115 are shown in FIG. 1 and three holes 115 are shown in FIG. 2, any number of holes may be used. Gloves 201 may be detachably sealed over holes 115 so that a user can reach into sealed enclosure 105 to manipulate a sample without breaching the seal. In other embodiments, sealed enclosure 105 may have other means for manipulating a sample, including but not limited to robotic arms 190, magnets, tongs, etc.

System 100 may further include a control system 120 for the sealed enclosure 105. Control system 120 may allow a user to control the conditions inside sealed enclosure 105, including but not limited to the power, temperature, air flow, light conditions, etc. Control system 120 may also be able to visually and/or audibly alert a user to any problems within sealed enclosure 105.

Sealed enclosure 105 may be coupled to a filtration system 132. Filtration system 132 may draw ambient air into sealed enclosure 105 through inlet 125. Filtration system 132 may draw internal, possibly contaminated, air out of sealed enclosure 105 through outlet 130. Filtration system 132 maybe any type of filtration system known, but preferably, filtration system 132 may include one of a carbon gas filter and a high efficiency particulate air (HEPA) filter. In certain embodiments a gas waste stream can be vented directly back into the system.

System 100 is configured so that the majority of the analytical instruments can be placed outside sealed enclosure 105 with only the portion of each analytical instrument necessary to retrieve sample information being disposed within enclosure 105 and thereby exposed to the sample. Such instruments may include, but are not limited to, optical spectroscopic instrumentation for methods such as absorption, fluorescence, phosphorescence, scattering, emission, and chemiluminescence testing of the sample. In the embodiment shown in FIGS. 1 and 2, a Fourier transform infrared (FTIR) detector 135 and a Raman spectroscopy detector 140 are shown; however any instrument or combination of instruments may be used. FTIR detector 135 and Raman detector 140 are both shown coupled to the bottom face of sealed enclosure 105; however such instruments can be coupled to any face of sealed enclosure 105.

Figure 3:
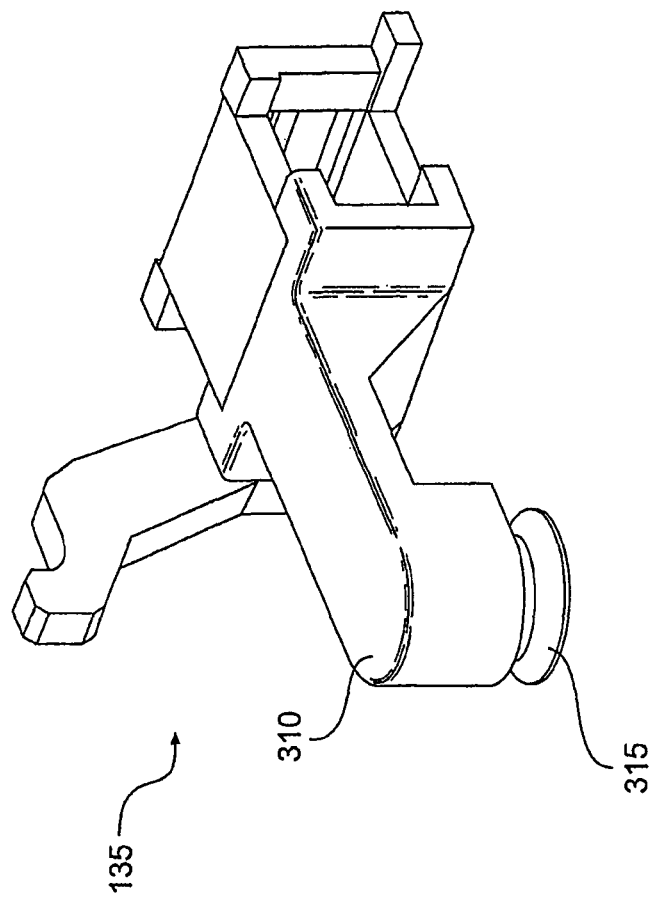
FIG. 3 is the interior portion of a FTIR detector.

FIG. 3 shows a close up view of the portion of FTIR detector 135 that is positioned inside sealed enclosure 105. The internal portion of the FTIR detector 135 may be coupled to the bottom face of sealed enclosure 105 so that a surface window 315 is pressed level with the floor of sealed enclosure 105 and the sample press 310 is tucked onto the back wall of sealed enclosure 105. Surface window 315 is comprised of a diamond Attenuated Total Reflectance (ATR) material. In such a configuration, the optics and electronics of the FTIR device are outside sealed enclosure 105 while interrogating a sample inside the enclosure.

Figure 4:
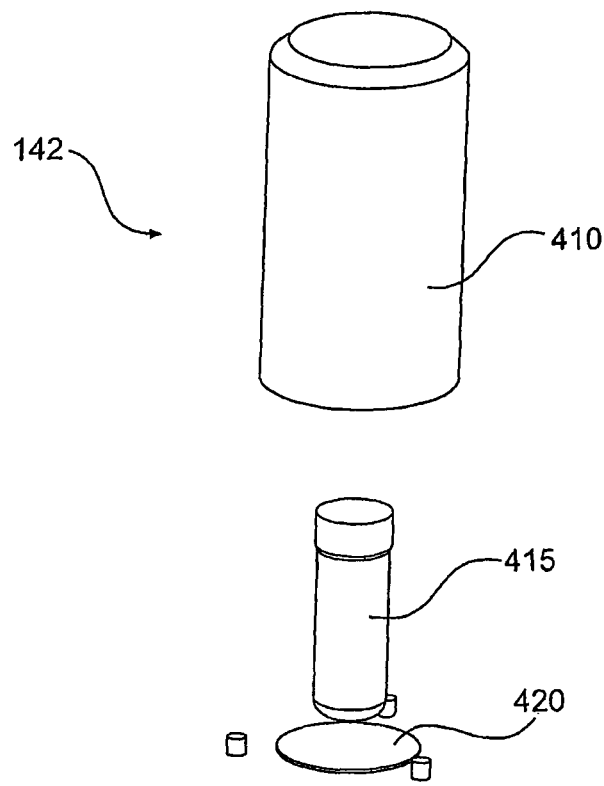
FIG. 4 is the interior portion of a Raman detector.

FIGS. 1 and 2 show the Raman spectroscopy detector 140 positioned outside enclosure 105. FIG. 4 shows a close up view of the portion of the Raman detection system 142 that is positioned inside sealed enclosure 105. The internal sampling portion of the Raman detector 140 comprises a sampling component 142 that is disposed within the sealed enclosure 105. Sampling component 142 preferably provides a light-tight enclosure 410 to surround a sample vial 415. Enclosure 410 may be continually bathed in filtered air. Sampling component 142 may be electronically interlocked with Raman detector 140 such that it will not allow a laser to activate when the door is open, thus preventing accidental injury. A laser window 420 may be a part of the bottom face of sealed enclosure 105 and wilt not come into contact with sample vial 415. For Raman spectroscopy the laser window 420 may simply be comprised of glass.

System 100 may further include a processor 180. The processor may control the instruments, process the analysis, and export the results. The processor may be controlled by a hands-free input device 145. Hands-free input device 145 may be a foot-operated mouse that allows the user to manipulate the sample while controlling the processor. The processor may be in communication with a display device 150. Display device 150 may be a flat screen monitor coupled to sealed enclosure 105. In certain embodiments, the rear face of sealed enclosure may be a second transparent face and display device 150 may be coupled to the outer surface of the second transparent face.

System 100 may also include an airlock 155. Airlock 155 may be coupled to any face of sealed enclosure 105. Airlock 155 may have an outer door 160 and an inner door 262 as shown in FIG. 2, each of which cannot be open while the other is open. While outer door 160 is shown on the end of airlock 155 in FIG. 1 and on the side of airlock 155 in FIG. 2, outer door 160 may be on any face of airlock 155. Airlock 155 may be removable and may be able to be stored inside sealed enclosure 105. Such storage would facilitate in transporting system 100. Airlock 155 provides a means for transferring items from outside enclosure 105 in inside enclosure 105 without loss of pressure differential within enclosure 105 and possible escape of contaminated air from inside enclosure 105.

A closed circuit video camera 192 may be mounted on a transparent face outside sealed enclosure 105. The closed circuit video camera 192 may also be mounted to an inner surface of sealed enclosure 105 so that the camera's field of view encompasses the work area of sealed enclosure 105. A microphone 195 may also be coupled to the sealed enclosure 105. The microphone 195 may be able to receive sounds from both within sealed enclosure 105 and from outside sealed enclosure 105. The camera 192 and microphone 195 may be in communication with the processor 180. The processor 180 may record data from the camera 192 and microphone 195 and may be able to relay the data to remote viewers, thereby allowing an analyst to direct remote viewers to aspects of the sample that may be deemed important.

Sealed enclosure 105 may have one or more removable panels. A removable panel may be replaced by an instrument mount 165. Instrument mount 165 may be able to house and contain additional analysis instruments, for example, including but not limited to gas analyzers. As in the embodiment of FIG. 2, analysis instruments 270 may alternatively be mounted above airlock 155.

Sealed enclosure 105 may further include a bar code reader 199 surface mounted in one face of sealed enclosure 105. The bar code reader 199 may be coupled to a sample management system. Furthermore system 100 may have a voice recognition system for describing observation and producing field notes in a rapid manner. In certain embodiments, biological robot devices can manipulate well plates and deliver them to the airlock 155 for sample inoculation and sealing.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. As used in the specification, the term "comprising" includes the terms "consisting of" and "consisting essentially of."

The invention claimed is:

1. A mobile analytical sample containment system, comprising:
   a sealed enclosure having at least one transparent face;
   a plurality of analytical instruments, each coupled to an outer surface of at least one face of the sealed enclosure, wherein only a sampling portion of each analytical instrument necessary to retrieve sample information is positioned inside and accessible from inside the sealed enclosure;
   at least one manipulation means for manipulating a sample contained within the sealed enclosure; and
   means for controlling the conditions within the sealed enclosure.

2. The mobile analytical sample containment system of claim 1, further comprising an air filtration system coupled to the sealed enclosure.

3. The mobile analytical sample containment system of claim 2, wherein the air filtration system contains at least one of a carbon gas filter and a high efficiency particulate air (HEPA) filter, and wherein said enclosure is maintained at a negative pressure relative to ambient pressure.

4. The mobile analytical sample containment system of claim 1, wherein the manipulation means is a manual manipulation means.

5. The mobile analytical sample containment system of claim 4, wherein the manual manipulation means comprises at least one glove coupled to a face of the sealed enclosure, wherein the glove passes through a hole in the face of the sealed enclosure and is sealed over the hole.

6. The mobile analytical sample containment system of claim 1, wherein the manipulation means is a robotic arm.

7. The mobile analytical sample containment system of claim 1, further comprising:
   a processing unit in communication with the plurality of analytical instruments; and
   a display unit for displaying data from the processing unit.

8. The mobile analytical sample containment system of claim 7, wherein the processing unit is controlled by a hands-free data entry unit.

9. The mobile analytical sample containment system of claim 8, wherein the hands-free data entry unit is a foot controlled mouse.

10. The mobile analytical sample containment system of claim 7, wherein the display unit is a monitor coupled to the sealed enclosure.

11. The mobile analytical sample containment system of claim 1, further comprising:

a close circuit video camera positioned so that a work surface of the sealed enclosure is within the field of view of the video camera; and a microphone.

12. The mobile analytical sample containment system of claim 1, further comprising a removable air-lock for transferring items into and out of said enclosure.

13. The mobile analytical sample containment system of claim 1, wherein at least one of the plurality of analytical instruments is chosen from the group consisting of a Fourier transform infrared (FTIR) detector and a Raman spectroscopy detector.

14. The mobile analytical sample containment system of claim 13, wherein the FTIR detector includes a surface window which forms a part of and is level with a surface of the sealed enclosure and wherein optical and electrical components of the FTIR are positioned outside of the sealed enclosure.

15. The mobile analytical sample containment system of claim 14, wherein the surface window comprises diamond attenuated total reflectance (ATR) material.

16. The mobile analytical sample containment system of claim 13, wherein the Raman detector has a sampling component within the sealed enclosure.

17. The mobile analytical sample containment system of claim 16, wherein the sampling component comprises a light sealed enclosure surrounding a sample vial which is bathed in carbon and HEPA filtered air.

18. The mobile analytical sample containment system of claim 17, wherein the Raman detector includes a laser window which forms a part of a surface of the sealed enclosure so that a laser can interrogate the sample vial while positioned outside the enclosure.

19. The mobile analytical sample containment system of claim 18, wherein said window is comprised of glass.

20. The mobile analytical sample containment system of claim 1, further comprising a barcode scanner embedded in a face of the sealed enclosure.

21. The mobile analytical sample containment system of claim 1, further comprising a removable instrument mount.

* * * * *